(12) United States Patent
Gibson et al.

(10) Patent No.: US 7,847,121 B2
(45) Date of Patent: *Dec. 7, 2010

(54) CARBOXYLIC ACID PRODUCTION PROCESS

(75) Inventors: Philip Edward Gibson, Kingsport, TN (US); Kenny Randolph Parker, Afton, TN (US)

(73) Assignee: Eastman Chemical Company, Kingsport, TN (US)

( * ) Notice: Subject to any disclaimer, the term of this patent is extended or adjusted under 35 U.S.C. 154(b) by 707 days.

This patent is subject to a terminal disclaimer.

(21) Appl. No.: 11/705,307

(22) Filed: Feb. 12, 2007

(65) Prior Publication Data

US 2007/0208195 A1    Sep. 6, 2007

Related U.S. Application Data

(60) Provisional application No. 60/777,799, filed on Mar. 1, 2006, provisional application No. 60/777,809, filed on Mar. 1, 2006, provisional application No. 60/777,810, filed on Mar. 1, 2006, provisional application No. 60/777,902, filed on Mar. 1, 2006.

(51) Int. Cl.
*C07C 51/42* (2006.01)

(52) U.S. Cl. .................. 562/485; 562/486; 562/487

(58) Field of Classification Search ................ 562/416, 562/417, 485, 486, 487
See application file for complete search history.

(56) References Cited

U.S. PATENT DOCUMENTS

| | | | |
|---|---|---|---|
| 3,931,305 A | 1/1976 | Fisher | |
| 4,158,738 A | 6/1979 | Scott et al. | |
| 4,219,669 A | 8/1980 | Tsuchiya et al. | |
| 4,330,676 A | 5/1982 | Moxham | |
| 4,356,319 A | 10/1982 | Roffia et al. | |
| 4,769,489 A | 9/1988 | Abrams et al. | |
| 4,792,621 A | 12/1988 | Abrams | |
| 4,914,230 A | 4/1990 | Abrams et al. | |
| 4,939,297 A | 7/1990 | Browder et al. | |
| 5,175,355 A | 12/1992 | Streich et al. | |
| 5,200,557 A | 4/1993 | Gee et al. | |
| 5,470,473 A | 11/1995 | Park et al. | |

(Continued)

FOREIGN PATENT DOCUMENTS

DE    10 2004002962    8/2005

(Continued)

OTHER PUBLICATIONS

Copending U.S. Appl. No. 11/708,200, filed Feb. 20, 2007, Kenny Randolph Parker et al.

(Continued)

*Primary Examiner*—Taylor Victor Oh
(74) *Attorney, Agent, or Firm*—Steven A. Owen; Bernard J. Graves, Jr.

(57) ABSTRACT

Disclosed are processes and apparatus for producing a carboxylic acid. The processes employ a concentration section disposed before and/or after a product isolation section, which allows for oxidation byproducts produced in the process to exit the product isolation section with the isolated carboxylic acid product and/or to be combined with the isolated carboxylic acid product downstream of the product isolation section at a rate of at least about 15 percent of the net make rate of the oxidation byproducts in the production process.

24 Claims, 4 Drawing Sheets

U.S. PATENT DOCUMENTS

Figure 1:
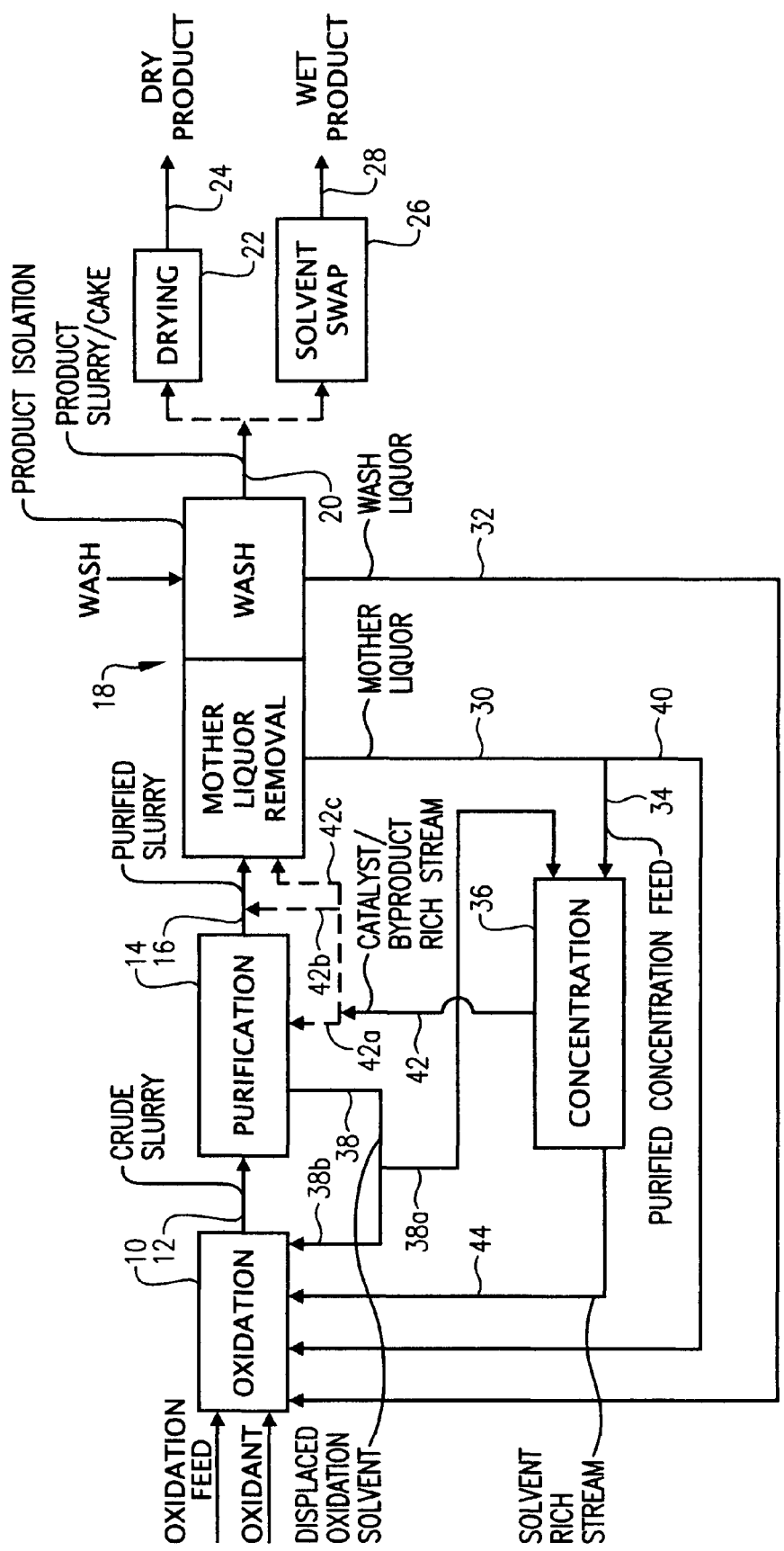

| | | | |
|---|---|---|---|
| 5,583,254 | A | 12/1996 | Turner |
| 5,643,468 | A | 7/1997 | Ure |
| 5,676,847 | A | 10/1997 | Yamamoto |
| 5,698,734 | A * | 12/1997 | Turner et al. ............... 562/412 |
| 5,705,682 | A | 1/1998 | Ohkashi et al. |
| 5,770,765 | A | 6/1998 | Ohkashi |
| 5,777,161 | A * | 7/1998 | Inary ..................... 562/485 |
| 5,840,965 | A | 11/1998 | Turner et al. |
| 5,877,346 | A | 3/1999 | Hindmarsh et al. |
| 5,971,907 | A | 10/1999 | Johannemann et al. |
| 6,150,553 | A | 11/2000 | Parten |
| 6,307,099 | B1 | 10/2001 | Turner et al. |
| 6,355,835 | B1 | 3/2002 | Kulsrestha et al. |
| 6,562,997 | B2 | 5/2003 | Sikkenga et al. |
| 6,639,104 | B2 | 10/2003 | Piras et al. |
| 6,655,531 | B1 | 12/2003 | Beard et al. |
| 6,765,113 | B2 | 7/2004 | Graham et al. |
| 7,074,954 | B2 | 7/2006 | Sheppard et al. |
| 7,132,566 | B2 | 11/2006 | Sumner, Jr. et al. |
| 7,193,109 | B2 | 3/2007 | Lin et al. |
| 7,196,215 | B2 * | 3/2007 | Lin et al. ................... 562/486 |
| 2002/0016500 | A1 | 2/2002 | Matsumoto et al. |
| 2003/0004372 | A1 | 1/2003 | Piras et al. |
| 2004/0110980 | A1 | 6/2004 | Sheppard et al. |
| 2004/0191139 | A1 | 9/2004 | Numata et al. |
| 2004/0244536 | A1 | 12/2004 | Lin |
| 2004/0245176 | A1 | 12/2004 | Parker et al. |
| 2004/0249208 | A1 | 12/2004 | Lin et al. |
| 2005/0159578 | A1 | 7/2005 | Parker et al. |
| 2005/0283022 | A1 | 12/2005 | Sheppard |
| 2006/0047165 | A1 | 3/2006 | Lin et al. |
| 2007/0205153 | A1 | 9/2007 | Parker et al. |
| 2007/0208199 | A1 | 9/2007 | Parker et al. |
| 2007/0208200 | A1 | 9/2007 | Parker et al. |

FOREIGN PATENT DOCUMENTS

| | | |
|---|---|---|
| EP | 0406424 | 1/1991 |
| EP | 0630673 | 12/1994 |
| WO | WO 00/63146 | 10/2000 |
| WO | WO 01/49647 | 7/2001 |
| WO | WO 01/55075 | 8/2001 |

OTHER PUBLICATIONS

Copending U.S. Appl. No. 11/708,245, filed Feb. 20, 2007, Kenny Randolph Parker et al.
Copending U.S. Appl. No. 11/705,330, filed Feb. 12, 2007, Philip Edward Gibson et al.
PCT International Search Report for corresponding application.
USPTO Office Action dated Sep. 24, 2007 for copending U.S. Appl. No. 11/708,200.
USPTO Office Action dated Mar. 17, 2008 for copending U.S. Appl. No. 11/708,200.
USPTO Notice of Allowance dated Oct. 28, 2008 for copending U.S. Appl. No. 11/708,200.
USPTO Office Action dated Oct. 15, 2009 for copending U.S. Appl. No. 11/705,330.
USPTO Office Action dated Nov. 2, 2009 for copending U.S. Appl. No. 11/708,245.
USPTO Office Action dated Jun. 8, 2010 for copending U.S. Appl. No. 11/705,330.

* cited by examiner

CARBOXYLIC ACID PRODUCTION PROCESS

RELATED APPLICATIONS

This application claims the priority benefit of U.S. Provisional Pat. App. Serial Nos. 60/777,799; 60/777,809; 60/777,810; and 60/777,902, all filed Mar. 1, 2006, the entire disclosures of which are incorporated herein by reference.

BACKGROUND OF THE INVENTION

1. Field of the Invention

The present invention relates generally to a carboxylic acid production process in which a concentration step is employed before and/or after a product isolation step. More specifically, the present invention concerns a process for the production of a terephthalic acid product where oxidation byproducts exit a product isolation step with isolated solids comprising terephthalic acid at a rate of at least about 15 percent of the net make rates of the oxidation byproducts in the production process.

2. Description of the Prior Art

In conventional terephthalic acid (TPA) production processes, para-xylene undergoes oxidation. In such processes, oxidation byproducts are produced along with the formation of TPA. Typically, such oxidation byproducts include the oxidation intermediates and side reaction products formed in the oxidation of para-xylene, as well as any impurities originating from the raw materials. Some of these byproducts are detrimental to the use of TPA in various production processes, such as for the production of polyethylene terephthalate (PET), dimethyl terephthalate (DMT), or cyclohexane dimethanol (CHDM). For example, some oxidation byproducts can act as chain terminators in a PET polymerization process, thus decreasing the molecular weight of the PET product. Accordingly, conventional TPA production processes remove substantially all of the oxidation byproducts produced therein.

It is known in the art to employ a purge process to remove oxidation byproducts from TPA production processes. A purge process typically involves separating a portion of a mother liquor, generated from the separation of liquid from the product stream, to form a purge feed stream. The purge feed stream generally constitutes in the range of from 5 to 40 percent of the total mother liquor, but can be up to 100 percent of the mother liquor. In a typical conventional purge process, the purge feed stream contains acetic acid, catalyst, water, oxidation byproducts, and minor amounts of terephthalic acid. The purge feed stream in conventional processes is usually resolved into a catalyst rich stream and an oxidation byproduct rich stream. The catalyst rich stream is typically recycled to the oxidizer, whereas the oxidation byproduct rich stream is usually routed out of the TPA production process for waste treatment or destruction.

Despite the advantages gained from a purge process, concerns arise regarding employing a purge in a TPA production process due to the added cost of producing the TPA product. Additionally, the removal of oxidation byproducts decreases product yield, further increasing the cost of the final product. Accordingly, there is a need for a TPA production process wherein at least a portion of the oxidation byproducts exit the production process with the TPA product and/or are combined with the TPA product downstream of the process.

SUMMARY OF THE INVENTION

One embodiment of the present invention concerns a carboxylic acid production process comprising: (a) treating a concentration feed stream comprising a solvent and solids in a concentration zone to thereby produce a solvent rich stream and a concentrated isolation feed stream comprising the solids; and (b) isolating at least a portion of the solids from the concentrated isolation feed stream in a product isolation zone to thereby produce a mother liquor and an isolated product comprising isolated solids, wherein the isolated solids comprise carboxylic acid particles and oxidation byproducts, wherein the oxidation byproducts are formed in the production process, wherein the rate at which the oxidation byproducts exit the product isolation zone with the isolated solids is at least about 75 percent of the net make rate of the oxidation byproducts in the production process.

Another embodiment of the present invention concerns a terephthalic acid production process comprising: (a) oxidizing an aromatic compound in an oxidation zone to thereby produce a crude product stream; (b) purifying the crude product stream in a purification zone to thereby produce a purified product stream comprising solvent and solid particles comprising terephthalic acid and oxidation byproducts; (c) concentrating the purified product stream in a concentration zone to thereby produce a concentrated isolation feed stream comprising at least a portion of the solid particles; and (d) treating the concentrated isolation feed stream in a product isolation zone to thereby produce a mother liquor and an isolated product comprising at least a portion of the solid particles, wherein substantially all of the oxidation byproducts entering the product isolation zone exit the product isolation zone with the isolated product and/or are returned, either directly or indirectly, to a point in the production process upstream of the product isolation zone.

Still another embodiment of the present invention concerns A terephthalic acid production process comprising: (a) oxidizing an aromatic compound in an oxidation section to thereby produce a crude terephthalic acid stream; (b) treating the crude terephthalic acid stream in a post-oxidation section to thereby produce a purified terephthalic acid stream comprising solvent, solid particles of purified terephthalic acid, and oxidation byproducts; (c) concentrating the purified terephthalic acid stream in a concentration section to thereby produce a concentrated stream; and (d) treating at least a portion of the concentrated stream in a catalyst removal section to thereby produce a mother liquor stream and a terephthalic acid product, wherein the rate at which the oxidation byproducts exit the process with the terephthalic acid product is substantially the same as the make rate of the oxidation byproducts in the process.

BRIEF DESCRIPTION OF THE DRAWING FIGURES

Figure 2:
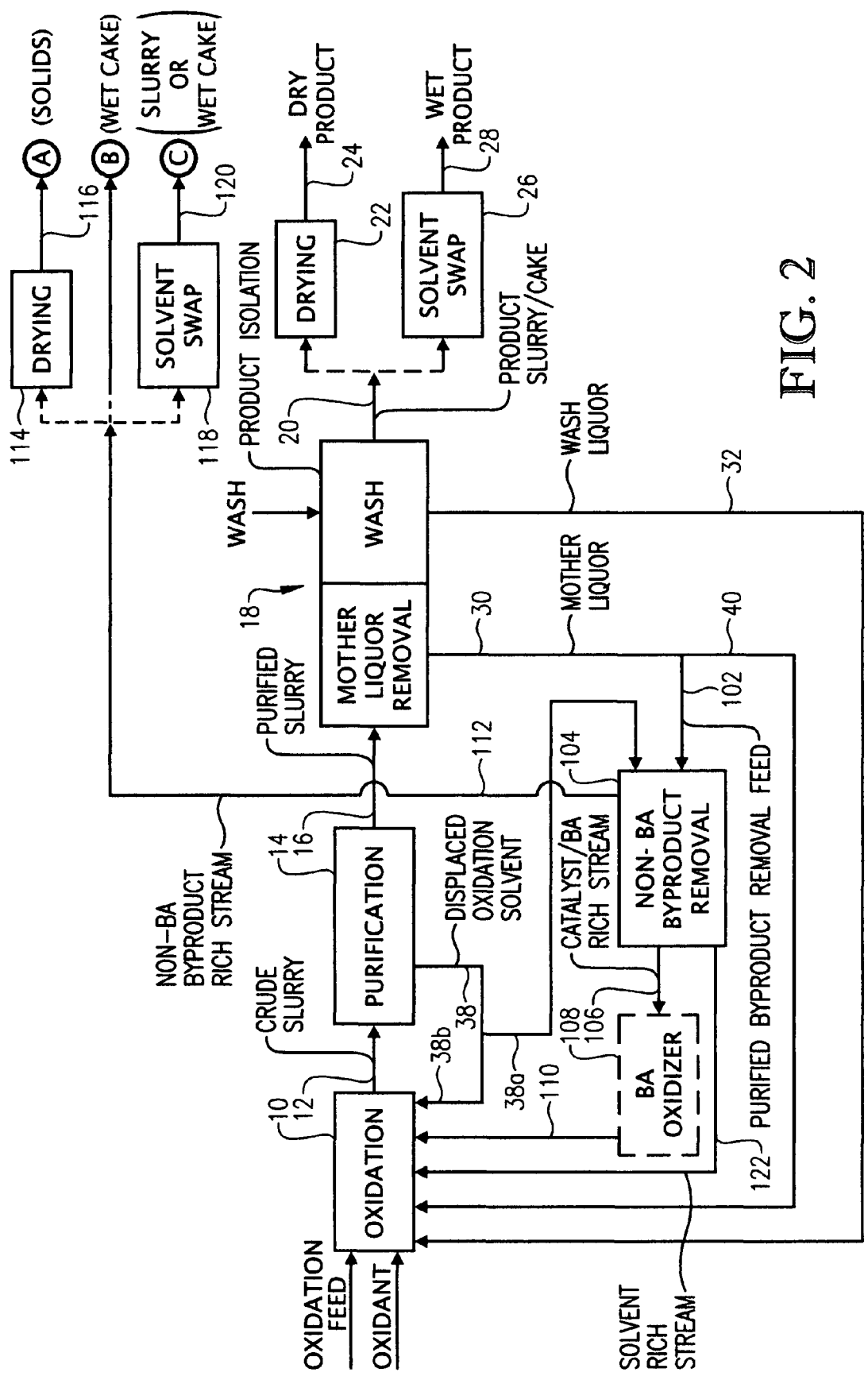
Figure 3:
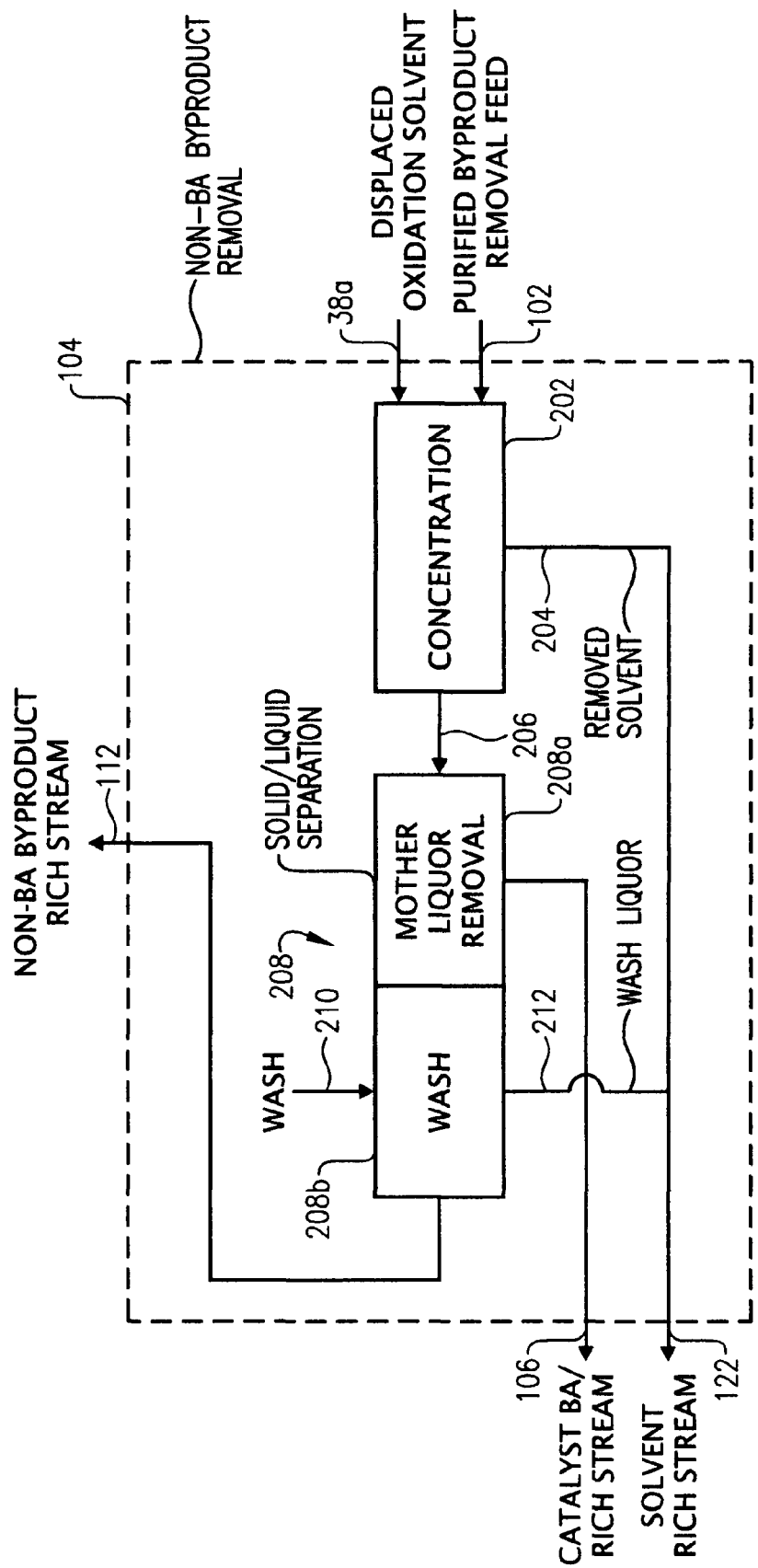
Figure 4:
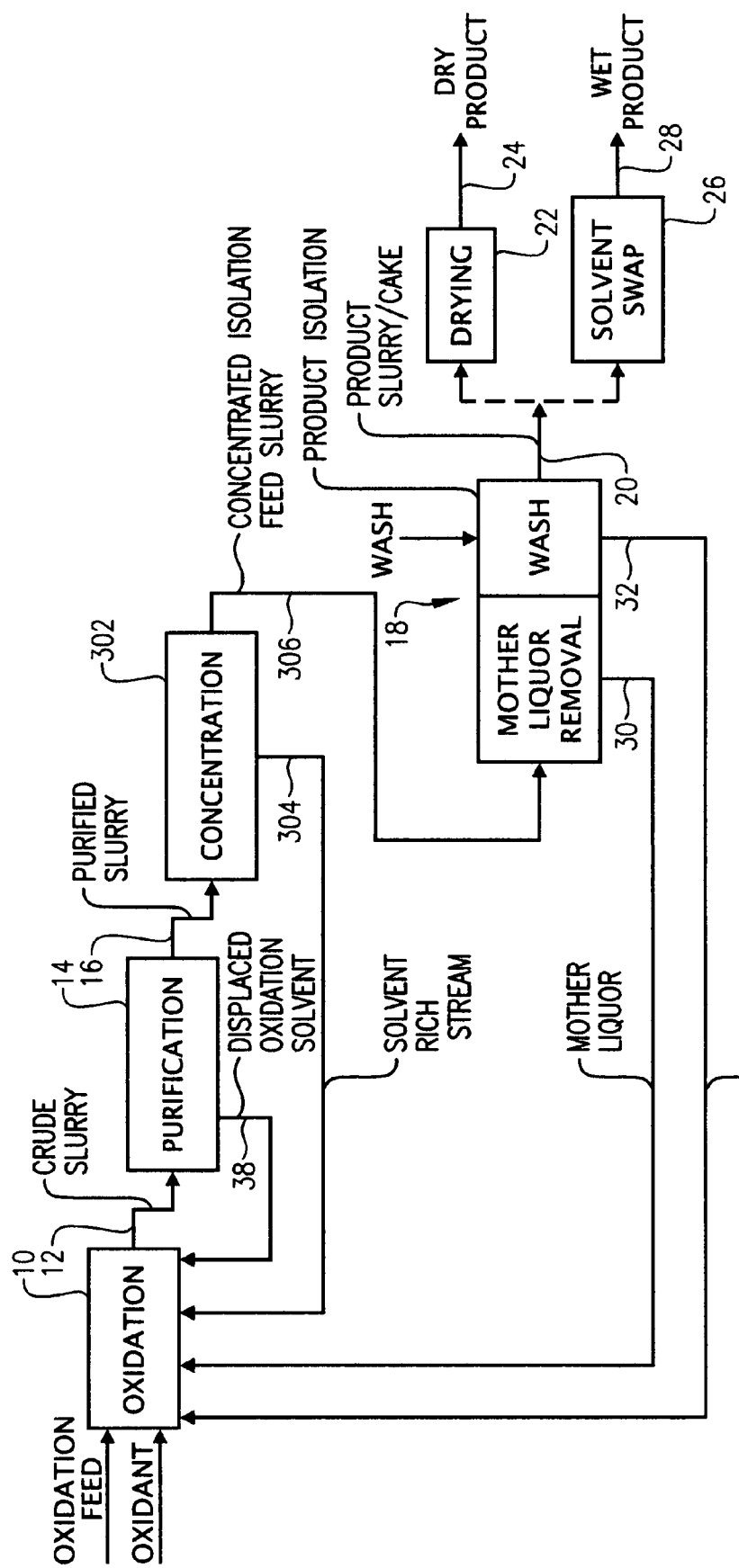

A preferred embodiment of the present invention is described in detail below with reference to the attached drawing figures, wherein:

FIG. 1 is a process flow diagram illustrating a system for the production and purification of carboxylic acid constructed in accordance with a first embodiment of the present invention, particularly illustrating a configuration where the crude slurry from the oxidation reactor is subjected to purification, the resulting purified slurry is subjected to product isolation, and a portion of the displaced oxidation solvent from the purification zone and a portion of the mother liquor from the product isolation zone are employed as feeds to a concentration zone;

FIG. 2 is a process flow diagram illustrating a system for the production and purification of carboxylic acid constructed in accordance with a second embodiment of the present invention, particularly illustrating a configuration where the crude slurry from the oxidation reactor is subjected to purification, the resulting purified slurry is subjected to product isolation, and a portion of the displaced oxidation solvent from the purification zone and a portion of the mother liquor from the product isolation zone are employed as feeds to a non-BA byproduct removal zone;

FIG. 3 is a process flow diagram illustrating in detail a non-BA byproduct removal zone constructed in accordance with the second embodiment of the present invention, particularly illustrating a configuration where the displaced oxidation solvent and the purified byproduct removal feed are subjected to concentration, and the resulting concentrated stream is subjected to solid/liquid separation; and FIG. 4 is a process flow diagram illustrating a system for the production and purification of carboxylic acid constructed in accordance with a third embodiment of the present invention, particularly illustrating a configuration where the crude slurry from the oxidation reactor is subjected to purification, the resulting purified slurry is subjected to concentration, the resulting solvent rich stream is returned to the oxidation reactor and the concentrated isolation feed slurry is subjected to product isolation.

DETAILED DESCRIPTION

FIG. 1 illustrates a carboxylic acid production process of the present invention where carboxylic acid produced in an oxidation reactor and purified in a purification reactor is subjected to product isolation. A portion of the resulting mother liquor from the product isolation zone can be treated in a concentration zone and resolved into a catalyst and byproduct rich stream and a solvent rich stream. As used herein, a "carboxylic acid production process" is defined as beginning with an initial oxidation step and ending with an isolated product, and can include therein one or more purification steps, concentration steps, isolation steps, and/or additional oxidation steps.

In the embodiment illustrated in FIG. 1, a predominately fluid-phase feed stream containing an oxidizable compound (e.g., para-xylene), a solvent (e.g., acetic acid and/or water), and a catalyst system (e.g., cobalt, manganese, and/or bromine) can be introduced into oxidation zone 10. A predominately gas-phase oxidant stream containing molecular oxygen can also be introduced into oxidation zone 10. The fluid- and gas-phase feed streams form a multi-phase reaction medium in oxidation zone 10. The oxidizable compound can undergo partial oxidation in a liquid phase of the reaction medium contained in oxidation zone 10.

In one embodiment of the present invention, oxidation zone 10 can comprise an agitated reactor. Agitation of the reaction medium in oxidation zone 10 can be provided by any means known in the art. As used herein, the term "agitation" shall denote work dissipated into the reaction medium causing fluid flow and/or mixing. In one embodiment, oxidation zone 10 can be a mechanically-agitated reactor equipped with means for mechanically agitating the reaction medium. As used herein, the term "mechanical agitation" shall denote agitation of the reaction medium caused by physical movement of a rigid or flexible element(s) against or within the reaction medium. For example, mechanical agitation can be provided by rotation, oscillation, and/or vibration of internal stirrers, paddles, vibrators, or acoustical diaphragms located in the reaction medium. In another embodiment of the present invention, oxidation zone 10 can comprise a bubble column reactor. As used herein, the term "bubble column reactor" shall denote a reactor for facilitating chemical reactions in a multi-phase reaction medium, wherein agitation of the reaction medium is provided primarily by the upward movement of gas bubbles through the reaction medium. As used herein, the terms "majority," "primarily," and "predominately" shall mean more than 50 percent.

The oxidizable compound present in the fluid-phase feed stream introduced into oxidation zone 10 can comprise at least one hydrocarbyl group. Also, the oxidizable compound can comprise an aromatic compound. In one embodiment, the oxidizable compound can comprise an aromatic compound with at least one attached hydrocarbyl group or at least one attached substituted hydrocarbyl group or at least one attached heteroatom or at least one attached carboxylic acid function (—COOH). In another embodiment, the oxidizable compound can comprise an aromatic compound with at least one attached hydrocarbyl group or at least one attached substituted hydrocarbyl group with each attached group comprising from 1 to 5 carbon atoms. In yet another embodiment, the oxidizable compound can be an aromatic compound having exactly two attached groups with each attached group comprising exactly one carbon atom and consisting of methyl groups and/or substituted methyl groups and/or at most one carboxylic acid group. Suitable examples of the oxidizable compound include, but are not limited to, para-xylene, meta-xylene, para-tolualdehyde, meta-tolualdehyde, para-toluic acid, and/or meta-toluic acid. In one embodiment of the present invention, the oxidizable compound comprises para-xylene.

A "hydrocarbyl group," as defined herein, is at least one carbon atom that is bonded only to hydrogen atoms and/or to other carbon atoms. A "substituted hydrocarbyl group," as defined herein, is at least one carbon atom bonded to at least one heteroatom and to at least one hydrogen atom. "Heteroatoms," as defined herein, are all atoms other than carbon and hydrogen atoms. "Aromatic compounds," as defined herein, comprise an aromatic ring and can comprise at least 6 carbon atoms and can also comprise only carbon atoms as part of the ring. Suitable examples of such aromatic rings include, but are not limited to, benzene, biphenyl, terphenyl, naphthalene, and other carbon-based fused aromatic rings.

The amount of oxidizable compound present in the fluid-phase feed stream introduced into oxidation zone 10 can be in the range of from about 4 to about 20 weight percent, or in the range of from 6 to 15 weight percent.

The solvent present in the fluid-phase feed stream introduced into primary oxidation reactor 10 can comprise an acid component and a water component. The solvent can be present in the fluid-phase feed stream at a concentration in the range of from about 60 to about 98 weight percent, in the range of from about 80 to about 96 weight percent, or in the range of from 85 to 94 weight percent. The acid component of the solvent can be an organic low molecular weight mono-carboxylic acid having from 1 to 6 carbon atoms, or 2 carbon atoms. In one embodiment, the acid component of the solvent can comprise acetic acid. The acid component can make up at least about 75 weight percent of the solvent, at least about 80 weight percent of the solvent, or in the range of from 85 to 98 weight percent of the solvent, with the balance being water.

As mentioned above, the fluid-phase feed stream introduced into oxidation zone 10 can also include a catalyst system. The catalyst system can be a homogeneous, liquid-phase catalyst system capable of promoting at least partial oxidation of the oxidizable compound. Also, the catalyst system can comprise at least one multivalent transition metal. In one embodiment, the catalyst system can comprise cobalt, bromine, and/or manganese.

When cobalt is present in the catalyst system, the fluid-phase feed stream can comprise cobalt in an amount such that the concentration of cobalt in the liquid phase of the reaction medium is maintained in the range of from about 300 to about 6,000 parts per million by weight (ppmw), in the range of from about 700 to about 4,200 ppmw, or in the range of from 1,200 to 3,000 ppmw. When bromine is present in the catalyst system, the fluid-phase feed stream can comprise bromine in an amount such that the concentration of bromine in the liquid phase of the reaction medium is maintained in the range of from about 300 to about 5,000 ppmw, in the range of from about 600 to about 4,000 ppmw, or in the range of from 900 to 3,000 ppmw. When manganese is present in the catalyst system, the fluid-phase feed stream can comprise manganese in an amount such that the concentration of manganese in the liquid phase of the reaction medium is maintained in the range of from about 20 to about 1,000 ppmw, in the range of from about 40 to about 500 ppmw, or in the range of from 50 to 200 ppmw.

In one embodiment of the present invention, cobalt and bromine can both be present in the catalyst system. The weight ratio of cobalt to bromine (Co:Br) in the catalyst system can be in the range of from about 0.25:1 to about 4:1, in the range of from about 0.5:1 to about 3:1, or in the range of from 0.75:1 to 2:1. In another embodiment, cobalt and manganese can both be present in the catalyst system. The weight ratio of cobalt to manganese (Co:Mn) in the catalyst system can be in the range of from about 0.3:1 to about 40:1, in the range of from about 5:1 to about 30:1, or in the range of from 10:1 to 25:1.

During oxidation, the oxidizable compound (e.g., para-xylene) can be continuously introduced into oxidation zone 10 at a rate of at least about 5,000 kilograms per hour, at a rate in the range of from about 10,000 to about 80,000 kilograms per hour, or in the range of from 20,000 to 50,000 kilograms per hour. During oxidation, the ratio of the mass flow rate of the solvent to the mass flow rate of the oxidizable compound entering oxidation zone 10 can be maintained in the range of from about 2:1 to about 50:1, in the range of from about 5:1 to about 40:1, or in the range of from 7.5:1 to 25:1.

The predominately gas-phase oxidant stream introduced into oxidation zone 10 can comprise in the range of from about 5 to about 40 mole percent molecular oxygen, in the range of from about 15 to about 30 mole percent molecular oxygen, or in the range of from 18 to 24 mole percent molecular oxygen. The balance of the oxidant stream can be comprised primarily of a gas or gases, such as nitrogen, that are inert to oxidation. In one embodiment, the oxidant stream consists essentially of molecular oxygen and nitrogen. In another embodiment, the oxidant stream can be dry air that comprises about 21 mole percent molecular oxygen and about 78 to about 81 mole percent nitrogen. In an alternative embodiment of the present invention, the oxidant stream can comprise substantially pure oxygen.

During liquid-phase oxidation in oxidation zone 10, the oxidant stream can be introduced into oxidation zone 10 in an amount that provides molecular oxygen somewhat exceeding the stoichiometric oxygen demand. Thus, the ratio of the mass flow rate of the oxidant stream (e.g., air) to the mass flow rate of the oxidizable compound (e.g., para-xylene) entering oxidation zone 10 can be maintained in the range of from about 0.5:1 to about 20:1, in the range of from about 1:1 to about 10:1, or in the range of from 2:1 to 6:1.

The liquid-phase oxidation reaction carried out in oxidation zone 10 can be a precipitating reaction that generates solids. In one embodiment, the liquid-phase oxidation reaction carried out in oxidation zone 10 can cause at least about 10 weight percent of the oxidizable compound (e.g., para-xylene) introduced into oxidation zone 10 to form solids (e.g., crude terephthalic acid (CTA) particles) in the reaction medium. In another embodiment, the liquid-phase oxidation carried out in oxidation zone 10 can cause at least about 50 weight percent of the oxidizable compound (e.g., para-xylene) introduced into oxidation zone 10 to form solids (e.g., CTA particles) in the reaction medium. In yet another embodiment, the liquid-phase oxidation carried out in oxidation zone 10 can cause at least about 90 weight percent of the oxidizable compound (e.g., para-xylene) introduced into oxidation zone 10 to form solids (e.g., CTA particles) in the reaction medium. In one embodiment, the solids content of the reaction medium can be maintained in the range of from about 5 to about 40 weight percent, in the range of from about 10 to about 35 weight percent, or in the range of from 15 to 30 weight percent. As used herein, the term "solids content" shall denote the weight percent solids in a multi-phase mixture.

During oxidation in oxidation zone 10, the multi-phase reaction medium can be maintained at an elevated temperature in the range of from about 125 to about 200° C., in the range of from about 150 to about 180° C., or in the range of from 155 to 165° C. The overhead pressure in oxidation zone 10 can be maintained in the range of from about 1 to about 20 bar gauge (barg), in the range of from about 2 to about 12 barg, or in the range of from 4 to 8 barg.

In the embodiment of FIG. 1, a crude slurry (i.e., a crude product stream) can be withdrawn from an outlet of oxidation zone 10 via line 12. The solid phase of the crude slurry in line 12 can be formed primarily of solid particles of CTA. The liquid phase of the crude slurry in line 12 can be a liquid mother liquor comprising at least a portion of the solvent, one or more catalyst components, and minor amounts of dissolved terephthalic acid (TPA). The solids content of the crude slurry in line 12 can be the same as the solids content of the reaction medium in oxidation zone 10, discussed above.

In one embodiment of the present invention, the crude slurry in line 12 can comprise impurities. As used herein, the term "impurities" is defined as any substance other than TPA, solvent, catalyst, and water. Such impurities can include oxidation byproducts formed during the at least partial oxidation of the above-mentioned oxidizable compound (e.g., para-xylene) including, but not limited to, benzoic acid (BA), bromo-benzoic acid, bromo-acetic acid, isophthalic acid, trimellitic acid, 2,5,4'-tricarboxybiphenyl, 2,5,4'-tricarboxybenzophenone, para-toluic acid (p-TAc), 4-carboxybenzaldehyde (4-CBA), monocarboxyfluorenones, monocarboxyfluorenes, and/or dicarboxyfluorenones.

Subsequent to removal from oxidation zone 10, the crude slurry can be introduced into purification zone 14 via line 12. In one embodiment, the crude slurry can be treated in purification zone 14 such that the concentration of at least one of the above-mentioned impurities in the crude slurry is reduced, thereby producing a purified slurry (i.e., a purified product stream). Such reduction in the concentration of impurities in the TPA can be accomplished by oxidative digestion, hydrogenation, and/or dissolution/recrystallization.

In one embodiment of the present invention, the crude slurry fed to purification zone 14 can have a 4-CBA content of at least about 100 parts per million based on the weight of the solids in the crude slurry ($ppmw_{cs}$), in the range of from about 200 to about 10,000 $ppmw_{cs}$, or in the range of from 800 to 5,000 $ppmw_{cs}$. The crude slurry fed to purification zone 14 can have a p-TAc content of at least about 250 $ppmw_{cs}$, in the range of from about 300 to about 5,000 $ppmw_{cs}$, or in the range of from 400 to 1,500 $ppmw_{cs}$. The purified slurry exiting purification zone 14 can have a 4-CBA content of less than about 150 parts per million based on the weight of the solids in the purified slurry (ppmw$_{ps}$), less than about 100 ppmw$_{ps}$, or less than 50 ppmw$_{ps}$. The purified slurry exiting purification zone 14 can have a p-TAc content of less than about 300 ppmw$_{ps}$, less than about 200 ppmw$_{ps}$, or less than 150 ppmw$_{ps}$. In one embodiment, treatment of the crude slurry in purification zone 14 can cause the purified slurry exiting purification zone 14 to have a 4-CBA and/or p-TAc content that is at least about 50 percent less than the 4-CBA and/or p-TAc content of the crude slurry fed to purification zone 14, at least about 85 percent less, or at least 95 percent less. By way of illustration, if the 4-CBA content of the crude slurry fed to purification zone 14 is 200 ppmw$_{cs}$ and the 4-CBA content of the purified slurry exiting purification zone 14 is 100 ppmw$_{ps}$, then the 4-CBA content of the purified slurry is 50 percent less than the 4-CBA content of the crude slurry.

In one embodiment of the present invention, the crude slurry can be subjected to purification by oxidative digestion in purification zone 14. As used herein, the term "oxidative digestion" denotes a process step or steps where a feed comprising solid particles is subjected to oxidation under conditions sufficient to permit oxidation of at least a portion of the impurities originally trapped in the solid particles. Purification zone 14 can comprise one or more reactors or zones. In one embodiment, purification zone 14 can comprise one or more mechanically-agitated reactors. A secondary oxidant stream, which can have the same composition as the gas-phase oxidant stream fed to oxidation zone 10, can be introduced into purification zone 14 to provide the molecular oxygen required for oxidative digestion. Additional oxidation catalyst can be added if necessary. In an alternative embodiment of the present invention, a stream comprising hydrogen can be introduced into purification zone 14 for at least partial hydrogenation of the crude slurry.

When oxidative digestion is employed in purification zone 14, the temperature at which oxidative digestion is carried out can be at least about 10° C. greater than the temperature of oxidation in oxidation zone 10, in the range of from about 20 to about 80° C. greater, or in the range of from 30 to 50° C. greater. The additional heat required for the operation of purification zone 14 can be provided by supplying a vaporized solvent to purification zone 14 and allowing the vaporized solvent to condense therein. The oxidative digestion temperature in purification zone 14 can be maintained in the range of from about 180 to about 240° C., in the range of from about 190 to about 220° C., or in the range of from 200 to 210° C. The oxidative digestion pressure in purification zone 14 can be maintained in the range of from about 100 to about 350 pounds per square inch gauge (psig), in the range of from about 175 to about 275 psig, or in the range of from 185 to 225 psig.

In one embodiment of the present invention, purification zone 14 can include two digestion reactors/zones—an initial digester and a final digester. When purification zone 14 includes an initial digester and a final digester, the final digester can be operated at a lower temperature and pressure than the initial digester. In one embodiment, the operating temperature of the final digester can be at least about 2° C. lower than the operating temperature of the initial digester, or in the range of from about 5 to about 15° C. lower than the operating temperature of the initial digester. In one embodiment, the operating pressure of the final digester can be at least about 5 psig lower than the operating pressure of the initial digester, or in the range of from about 10 to about 50 psig lower than the operating pressure of the initial digester. The operating temperature of the initial digester can be in the range of from about 195 to about 225° C., in the range of from 205 to 215° C., or about 210° C. The operating pressure of the initial digester can be in the range of from about 215 to about 235 psig, or about 225 psig. The operating temperature of the final digester can be in the range of from about 190 to about 220° C., in the range of from 200 to 210° C., or about 205° C. The operating pressure of the final digester can be in the range of from about 190 to 210 psig, or about 200 psig.

In one embodiment of the present invention, purification zone 14 can comprise optional first and second solvent swap zones. Optional first and second solvent swap zones can operate to replace at least a portion of the existing solvent in a slurry with a replacement solvent. Equipment suitable for such replacement includes, but is not limited to, a decanter centrifuge followed by a reslurry with replacement solvent, a disc stack centrifuge, an advancing front crystallizer, or multiple decanter centrifuges with optional counter current washing. The replacement oxidation solvent can have substantially the same composition as the solvent introduced into oxidation zone 10, as described above.

In one embodiment, the crude slurry fed to purification zone 14 can be treated in the optional first solvent swap zone prior to purification of the crude slurry by the above-mentioned oxidative digestion. In another embodiment, a purified slurry resulting from oxidative digestion of the crude slurry can be treated in the optional second solvent swap zone.

Optionally, at least a portion of the displaced oxidation solvent from the optional first and/or second solvent swap zones can be discharged from purification zone 14 via line 38. At least a portion of the displaced oxidation solvent in line 38 can be routed to concentration zone 36 via line 38a and/or oxidation zone 10 via line 38b.

In another embodiment of the present invention, purification zone 14 can comprise an optional crystallization zone and/or an optional cooling zone. A purified slurry resulting from the above-mentioned oxidative digestion of the crude slurry can be treated in the optional crystallization zone to at least partially increase the particle size distribution of the purified slurry. Optional crystallization zone can comprise any equipment known in the art that can operate to increase the particle size distribution of the purified slurry. When an optional cooling zone is employed, the purified slurry can be cooled therein to a temperature in the range of from about 20 to about 195° C. When both a crystallization zone and a cooling zone are employed, the purified slurry can be treated first in the crystallization zone and subsequently in the cooling zone.

Referring again to FIG. 1, a purified slurry can be withdrawn from an outlet of purification zone 14 via line 16. The solid phase of the purified slurry can be formed primarily of purified solids comprising carboxylic acid (e.g., purified terephthalic acid (PTA)), while the liquid phase can be formed of a mother liquor. As used herein, the term "purified solids" is defined as solid particles that have been subjected to at least one purification step. The solids content of the purified slurry in line 16 can be in the range of from about 1 to about 50 percent by weight, in the range of from about 5 to about 40 weight percent, or in the range of from 20 to 35 weight percent. Additionally, the mother liquor of the purified slurry in line 16 can comprise a solvent (e.g., acetic acid and/or water).

In one embodiment of the present invention, at least a portion of the crude slurry in line 12 can be employed as a product isolation feed stream. In another embodiment, at least a portion of the purified slurry in line 16 can be employed as a product isolation feed stream. The product isolation feed stream can be introduced into product isolation zone (i.e., catalyst removal zone) 18. Product isolation zone 18 can isolate at least a portion of the solids from the product isolation feed stream, thereby forming a predominately fluid phase mother liquor and an isolated product comprising isolated solids. Product isolation zone 18 can comprise any method of solid/liquid separation known in the art that is capable of generating a mother liquor stream and an isolated product comprising isolated solids. In addition, it may be desirable for product isolation zone 18 to have the capability of washing the isolated product. Suitable equipment for use in product isolation zone 18 includes, but is not limited to, a pressure drum filter, a vacuum drum filter, a vacuum belt filter, multiple solid bowl centrifuges with optional counter current wash, or a perforated centrifuge.

In one embodiment of the present invention, a wash stream can be introduced into product isolation zone 18 to wash at least a portion of the isolated product generated in product isolation zone 18, thereby producing a washed isolated product. In one embodiment, the wash stream can comprise acetic acid and/or water. After washing the isolated product, the used wash liquor can be withdrawn from product isolation zone 18 via line 32, and at least a portion of the wash liquor can be routed, either directly or indirectly, to oxidation zone 10.

The above-mentioned isolated solids generated in product isolation zone 18 can be discharged via line 20. In one embodiment, the isolated solids can comprise solid particles comprising crude carboxylic acid (e.g., CTA). In another embodiment, the isolated solids can comprise purified solids comprising purified carboxylic acid (e.g., PTA). The isolated solids can also comprise oxidation byproducts. The types of oxidation byproducts in the isolated solids can be the same as the oxidation byproducts discussed above in relation to the crude slurry in line 12. The individual solid particles that make up the isolated solids can comprise concentrations of carboxylic acid and oxidation byproducts in any ratio. In other words, an individual solid particle in the isolated solids can be comprised completely of oxidation byproducts, completely of carboxylic acid, or any possible combination of carboxylic acid and oxidation byproducts.

In one embodiment of the present invention, the rate at which oxidation byproducts exit product isolation zone 18 with the isolated solids is at least about 15 percent, at least about 40 percent, at least about 60 percent, at least about 80 percent, or at least 90 percent of the net make rate of the oxidation byproducts in the carboxylic acid production process. As used herein, the term "net make rate" is defined as the difference between the mass per unit time of oxidation byproducts entering the oxidation step (e.g., oxidation zone 10) and the mass per unit time of oxidation byproducts exiting the purification step (e.g., purification zone 14) minus the mass per unit time of any additional step (e.g., BA oxidizer 108, discussed in greater detail below) in the carboxylic acid production process that results in the destruction and/or conversion of any oxidation byproducts. If no purification step is employed in the carboxylic acid production process, the term "net make rate" is defined as the difference between the mass per unit time of oxidation byproducts entering the oxidation step (e.g., oxidation zone 10) and the mass per unit time of oxidation byproducts exiting the oxidation step (e.g., oxidation zone 10) minus the mass per unit time of any additional step in the production process that results in the destruction and/or conversion of any oxidation byproducts. By way of illustration, in a production process where a purification step is employed, if oxidation byproducts enter the oxidation step of the production process at a rate of 50 kilograms per hour (kg/hr), oxidation byproducts exit the purification step at a rate of 150 kg/hr, and oxidation byproducts are destroyed and/or converted in an additional step at a rate of 25 kg/hr, then the net make rate of oxidation byproducts in the production process is 75 kg/hr. In one embodiment of the present invention, the net make rate of oxidation byproducts in the carboxylic acid production process can be at least about 5 kg/hr, in the range of from about 5 to about 20,000 kg/hr, in the range of from about 10 to about 10,000 kg/hr, or in the range of from 20 to 5,000 kg/hr.

In another embodiment, oxidation byproducts can additionally be combined with the isolated solids downstream of product isolation zone 18, such that the rate at which oxidation byproducts exit product isolation zone 18 with the isolated solids and/or are combined with the isolated solids downstream of product isolation zone 18 is at least about 15 percent, at least about 40 percent, at least about 60 percent, at least about 80 percent, or at least 90 percent of the net make rate of the oxidation byproducts in the carboxylic acid production process. In another embodiment, all of the oxidation byproducts generated in the production process can exit the carboxylic acid production process with the isolated product at rates at or near their respective make rates in the process. In another embodiment, substantially all of the oxidation byproducts that enter product isolation zone 18 can exit product isolation zone 18 with the isolated solids and/or can be returned, either directly or indirectly, to a point in the production process upstream of product isolation zone 18.

The above-mentioned isolated product can comprise a concentration of oxidation byproducts of at least about 500 ppmw. In another embodiment, the isolated product can comprise a concentration of oxidation byproducts in the range of from about 1,000 to about 100,000 ppmw, in the range of from about 3,000 to about 75,000 ppmw, or in the range of from about 5,000 to about 50,000 ppmw.

The isolated product in line 20 can be in the form of a wet cake. The wet cake can comprise in the range of from about 5 to about 30 weight percent liquid, in the range of from about 10 to about 25 weight percent liquid, or in the range of from 12 to 23 weight percent liquid.

In one embodiment of the present invention, the isolated product in line 20 can optionally be introduced into drying zone 22 via line 20 to thereby produce a dried particulate product comprising isolated solids as discussed above. Drying zone 22 can comprise any drying device known in the art that can produce a dried isolated product comprising less than about 5 weight percent liquid, less than about 3 weight percent liquid, or less than 1 weight percent liquid. The dried isolated product can be discharged from drying zone 22 via line 24.

In another embodiment, the isolated product in line 20 can optionally be introduced into solvent swap zone 26 to produce a wet isolated product comprising isolated solids as discussed above. Solvent swap zone 26 can operate to replace at least a portion of the liquid in the isolated product with a replacement solvent. Equipment suitable for such replacement includes, but is not limited to, a decanter centrifuge followed by a reslurry with replacement solvent, a disc stack centrifuge, an advancing front crystallizer, or multiple decanter centrifuges with counter current washing. The wet isolated product can be discharged from solvent swap zone 26 via line 28. The wet isolated product can comprise in the range of from about 5 to about 30 weight percent liquid, in the range of from about 10 to about 25 weight percent liquid, or in the range of from 12 to 23 weight percent liquid.

Referring still to FIG. 1, the above-mentioned mother liquor can be discharged from product isolation zone 18 via line 30. In one embodiment of the present invention, at least a portion of the mother liquor in line 30 can be withdrawn from line 30 via line 34 to form a purified concentration feed stream, which can be fed to concentration zone 36. The amount of mother liquor withdrawn by line 34 to form the purified concentration feed stream can be in the range of from about 1 to about 55 percent of the total weight of the mother liquor, in the range of from about 5 to about 45 percent by weight, or in the range of from 10 to 35 percent by weight. As mentioned above, at least a portion of the displaced oxidation solvent discharged from purification zone 14 in line 38 can be introduced into concentration zone 36 via line 38a. Alternatively, the displaced oxidation solvent in line 38a can be combined with the purified concentration feed stream in line 34 prior to being introduced into concentration zone 36.

In another embodiment, at least a portion of the remaining mother liquor in line 30 can be routed, either directly or indirectly, to oxidation zone 10 via line 40. Optionally, at least a portion of the wash liquor in line 32 can be combined with at least a portion of the mother liquor in line 40 prior to introduction into oxidation zone 10.

In one embodiment of the present invention, the mother liquor in line 30, and consequently the purified concentration feed in line 34, can comprise solvent, one or more catalyst components, oxidation byproducts, and TPA. The solvent in the mother liquor in line 30 and the purified concentration feed in line 34 can comprise a monocarboxylic acid. In one embodiment, the solvent can comprise water and/or acetic acid. The mother liquor in line 30 and the purified concentration feed stream in line 34 can comprise solvent in an amount of at least about 85 weight percent, at least about 95 weight percent, or at least 99 weight percent.

The catalyst components in the mother liquor in line 30 and the purified concentration feed stream in line 34 can comprise the catalyst components as described above with reference to the catalyst system introduced into oxidation zone 10. In one embodiment, the catalyst components can comprise cobalt, manganese, and/or bromine. The mother liquor in line 30 and the purified concentration feed stream in line 34 can have a cumulative concentration of all of the catalyst components in the range of from about 500 to about 20,000 ppmw, in the range of from about 1,000 to about 15,000 ppmw, or in the range of from 1,500 to 10,000 ppmw.

The oxidation byproducts in the mother liquor in line 30 and the purified concentration feed stream in line 34 can comprise one or more of the oxidation byproducts discussed above. In one embodiment, the mother liquor in line 30 and the purified concentration feed stream in line 34 can have a cumulative concentration of all of the oxidation byproducts in the range of from about 1,000 to about 200,000 ppmw based on the weight of the purified concentration feed stream, in the range of from about 2,000 to about 120,000 ppmw, or in the range of from 3,000 to about 60,000 ppmw.

In one embodiment, the oxidation byproducts in the mother liquor in line 30 and the purified concentration feed stream in line 34 can comprise both BA and non-BA byproducts. As used herein, the term "non-BA byproducts" is defined as any oxidation byproduct that is not benzoic acid. Non-BA byproducts include, but are not limited to, isophthalic acid (IPA), phthalic acid (PA), trimellitic acid, 2,5,4'-tricarboxybiphenyl, 2,5,4'-tricarboxybenzophenone, p-TAc, 4-CBA, naphthalene dicarboxylic acid, monocarboxyfluorenones, monocarboxyfluorenes, and/or dicarboxyfluorenones. In one embodiment, the mother liquor in line 30 and the purified concentration feed stream in line 34 can comprise BA in an amount in the range of from about 500 to about 150,000 ppmw based on the weight of the purified concentration feed stream, in the range of from about 1,000 to about 100,000 ppmw, or in the range of from 2,000 to 50,000 ppmw. Additionally, the mother liquor in line 30 and the purified concentration feed stream in line 34 can have a cumulative concentration of non-BA byproducts in the range of from about 500 to about 50,000 ppmw, in the range of from about 1,000 to about 20,000 ppmw, or in the range of from 2,000 to 10,000 ppmw.

In one embodiment of the present invention, less than about 85 weight percent, less than about 50 weight percent, less than about 25 weight percent, less than about 5 weight percent, less than about 3 weight percent, or less than 1 weight percent of the oxidation byproducts in the mother liquor in line 30 are purged from the carboxylic acid production process. In another embodiment, no purge process is employed in the carboxylic acid production process. As used herein, the term "purge process" is defined as any process step or steps that treats a stream containing liquids and/or solids to remove any portion of the oxidation byproducts produced in the carboxylic acid production process in such a way that the removed oxidation byproducts do not exit the carboxylic acid production process with the carboxylic acid product produced therein and/or are not combined with the carboxylic acid product downstream of the carboxylic acid production process.

In one embodiment of the present invention, the mother liquor in line 30 and the purified concentration feed stream in line 34 can comprise solids in an amount of less than about 5 weight percent, less than about 2 weight percent, or less than 1 weight percent. Additionally, the purified concentration feed stream can have a temperature of less than about 240° C., in the range of from about 20 to about 200° C., or in the range of from 50 to 100° C.

Referring still to FIG. 1, as mentioned above, the purified concentration feed stream can be introduced into concentration zone 36 via line 34. Concentration zone 36 can separate the purified concentration feed stream and optionally the displaced oxidation solvent from line 38a into a catalyst and byproduct rich stream and a solvent rich stream.

Separation in concentration zone 36 can be achieved by any means known in the art that can remove at least a portion of the above-mentioned solvent from the non-solvent components (e.g., catalyst and oxidation byproducts) in the purified concentration feed stream. Examples of suitable equipment for use in concentration zone 36 include, but are not limited to, one or more evaporators. In one embodiment, concentration zone 36 can comprise at least two evaporators. When two evaporators are employed, each one individually can be operated under vacuum at reduced temperature, or can be operated at elevated temperature and pressure. In one embodiment, each evaporator can be operated at a temperature in the range of from about 40 to about 180° C. and a pressure in the range of from about 50 to about 4,500 torr during concentration. Suitable equipment for use as evaporators in concentration zone 36 can include, but is not limited to, a simple agitated and heated tank, a flash evaporator, an advancing front crystallizer, a thin film evaporator, a scraped thin film evaporator, a falling film evaporator, and/or a LIST dryer.

The catalyst and byproduct rich stream can be withdrawn from concentration section 36 via line 42. In one embodiment, the catalyst and byproduct rich stream in line 42 can have a cumulative concentration of all of the catalyst components and oxidation byproducts that is at least about 2 times, at least about 4 times, or at least 6 times the cumulative concentration of all of the catalyst components and oxidation byproducts in the purified concentration feed stream. The catalyst and byproduct rich stream in line 42 can have a cumulative concentration of all of the catalyst components of at least about 1,000 ppmw, in the range of from about 1,000 to about 120,000 ppmw, in the range of from about 2,000 to about 90,000 ppmw, or in the range of from 3,000 to 60,000 ppmw. Additionally, the catalyst and byproduct rich stream in line 42 can have a cumulative concentration of all of the oxidation byproducts of at least about 2,000 ppmw, in the range of from about 2,000 to about 900,000 ppmw, in the range of from about 4,000 to about 720,000 ppmw, or in the range of from 6,000 to 360,000 ppmw.

In one embodiment of the present invention, at least a portion of the catalyst and byproduct rich stream in line 42 can be routed to purification zone 14 via line 42a. When the catalyst and byproduct rich stream is routed to purification zone 14, the catalyst and byproduct rich stream can be introduced into either or both of the optional crystallization and cooling zones, discussed above in relation to purification zone 14. When the catalyst and byproduct rich stream is routed via line 42a, at least about 80 weight percent, at least about 90 weight percent, or at least 95 weight percent of the catalyst and byproduct rich stream can be introduced into purification zone 14. In one embodiment, substantially all of the catalyst components and oxidation byproducts in the catalyst and byproduct rich stream in line 42a can be introduced into purification zone 14.

In another embodiment, at least a portion of the catalyst and byproduct rich stream in line 42 can be introduced into the purified slurry in line 16 via line 42b. When the catalyst and byproduct rich stream is routed via line 42b, at least about 80 weight percent, at least about 90 weight percent, or at least 95 weight percent of the catalyst and byproduct rich stream can be introduced into line 16. In one embodiment, substantially all of the catalyst components and oxidation byproducts in the catalyst and byproduct rich stream in line 42b can be introduced into line 16.

In another embodiment, at least a portion of the catalyst and byproduct rich stream in line 42 can be introduced into product isolation zone 18 via line 42c. When the catalyst and byproduct rich stream is routed via line 42c, at least about 80 weight percent, at least about 90 weight percent, or at least 95 weight percent of the catalyst and byproduct rich stream can be introduced into product isolation zone 18. In one embodiment, substantially all of the catalyst components and oxidation byproducts in the catalyst and byproduct rich stream in line 42c can be introduced into product isolation zone 18.

The above-mentioned solvent rich stream can be withdrawn from concentration zone 36 via line 44. In one embodiment, the solvent rich stream can have a higher concentration of solvent than the concentration of solvent in the purified concentration feed stream in line 34. At least a portion of the solvent rich stream can be routed to oxidation zone 10 via line 44. In one embodiment, at least about 80 weight percent, at least about 90 weight percent, or at least 95 weight percent of the solvent rich stream in line 44 can be routed to oxidation zone 10.

FIG. 2 illustrates an embodiment of the present invention where a portion of the mother liquor in line 30 is withdrawn via line 102 to form a purified byproduct removal feed. The composition of the purified byproduct removal feed can be substantially the same as the composition of the purified concentration feed stream in line 34, as discussed above with reference to FIG. 1. The purified byproduct removal feed can be introduced into non-BA byproduct removal zone 104 via line 102. Additionally, a portion of the displaced oxidation solvent from purification zone 14 can be routed to non-BA byproduct removal zone 104 via line 38a or, alternatively, can be combined with the purified byproduct removal feed prior to introduction into non-BA byproduct removal zone 104. As will be discussed in greater detail below with reference to FIG. 3, non-BA byproduct removal zone 104 can separate the purified byproduct removal feed into a solvent rich stream, a catalyst and BA rich stream, and a non-BA byproduct rich stream.

The catalyst and BA rich stream can be withdrawn from non-BA byproduct removal zone 104 via line 106. In one embodiment, the catalyst and BA rich stream can have a cumulative concentration of all of the catalyst components and BA that is at least about 2 times, at least about 4 times, or at least 6 times the cumulative concentration of all of the catalyst components and BA in the purified byproduct removal feed. The catalyst and BA rich stream in line 106 can have a cumulative concentration of all of the catalyst components of at least about 1,000 ppmw, in the range of from about 1,000 to about 120,000 ppmw, in the range of from about 2,000 to about 90,000 ppmw, or in the range of from 3,000 to 60,000 ppmw. Additionally, the catalyst and BA rich stream in line 106 can have a concentration of BA of at least about 1,000 ppmw, in the range of from about 1,000 to about 900,000 ppmw, in the range of from about 2,000 to about 600,000 ppmw, or in the range of from 4,000 to about 300,000 ppmw.

In one embodiment, at least a portion of the catalyst and BA rich stream can be routed to optional BA oxidizer 108, where at least a portion of the BA in the catalyst and BA rich stream can be oxidized. BA oxidizer 108 can be any oxidation reactor capable of reducing the amount of BA in the catalyst and BA rich stream by at least about 10 weight percent, at least about 25 weight percent, or at least 50 weight percent.

An optionally oxidized catalyst and BA rich stream can be withdrawn from BA oxidizer 108 via line 110. The oxidized catalyst and BA rich stream in line 110 can have a concentration of BA in the range of from about 900 to about 810,000 ppmw, in the range of from about 1,500 to about 450,000 ppmw, or in the range of from 2,000 to 150,000 ppmw. At least a portion of the optionally oxidized catalyst and BA rich stream can be routed to oxidation zone 10 via line 110. In one embodiment, at least about 80 weight percent, at least about 90 weight percent, or at least 95 weight percent of the optionally oxidized catalyst and BA rich stream in line 110 can be introduced into oxidation zone 10.

The non-BA byproduct rich stream can be withdrawn from non-BA byproduct removal zone via line 112. In one embodiment, the non-BA byproduct rich stream can have a cumulative concentration of non-BA byproducts that is at least about 2 times, at least about 4 times, or at least about 6 times the cumulative concentration of non-BA byproducts in the purified byproduct removal feed. The non-BA byproduct rich stream in line 112 can have a cumulative concentration of non-BA byproducts of at least about 10 weight percent, in the range of from about 10 to about 95 weight percent, in the range of from about 20 to about 90 weight percent, or in the range of from 30 to about 85 weight percent.

The non-BA byproduct rich stream in line 112 can be in the form of a wet cake. In one embodiment, the non-BA byproduct rich stream in line 112 can comprise liquid in an amount in the range of from about 5 to about 30 weight percent, in the range of from about 10 to about 25 weight percent, or in the range of from about 12 to about 23 weight percent.

Optionally, the non-BA byproduct rich stream in line 112 can be introduced into drying zone 114. Drying zone 114 can comprise any drying device known in the art that can produce a dried non-BA byproduct rich stream comprising less than about 5 weight percent liquid, less than about 3 weight percent liquid, or less than 1 weight percent liquid. The dried non-BA byproduct rich stream can be discharged from drying zone 22 via line 24.

In another embodiment, the non-BA byproduct rich stream in line 112 can optionally be introduced into solvent swap zone 118 to produce a wet non-BA byproduct rich stream. Solvent swap zone 118 can operate to replace at least a portion of the liquid in the non-BA byproduct rich stream with a replacement solvent. Equipment suitable for such replacement includes, but is not limited to, a decanter centrifuge followed by a reslurry with replacement solvent, a disc stack centrifuge, an advancing front crystallizer, or multiple decanter centrifuges with counter current washing. The wet non-BA byproduct rich stream can be discharged from solvent swap zone 118 via line 120. The wet non-BA byproduct rich stream can comprise in the range of from about 5 to about 30 weight percent liquid, in the range of from about 10 to about 25 weight percent liquid, or in the range of from 12 to 23 weight percent liquid.

In one embodiment of the present invention, at least a portion of the non-BA byproduct rich stream can be combined with the isolated product in line 20, the dried isolated product in line 24, and/or the wet isolated product in line 28. In one embodiment, at least about 80 weight percent, at least about 90 weight percent, at least 95 weight percent, or substantially all of the non-BA byproducts in the non-BA byproduct rich stream can be combined with the isolated product in line 20, the dried isolated product in line 24, and/or the wet isolated product in line 28.

The solvent rich stream produced in non-BA byproduct removal zone 104 can be withdrawn via line 122. The solvent rich stream in line 122 can have a higher concentration of solvent than the concentration of solvent in the purified byproduct removal feed stream in line 102. In one embodiment, at least a portion of the solvent rich stream generated in non-BA byproduct removal zone 104 can be routed to oxidation zone 10 via line 122. At least about 80 weight percent, at least about 90 weight percent, or at least 95 weight percent of the solvent rich stream in line 122 can be introduced into oxidation zone 10.

FIG. 3 illustrates a detailed configuration of non-BA byproduct removal zone 104. In the embodiment of FIG. 3, non-BA byproduct removal zone 104 comprises concentration section 202 and solid/liquid separation section 208. In this embodiment, the purified byproduct removal feed can initially be introduced into concentration section 202 via line 102. Optionally, as mentioned above, at least a portion of the displaced oxidation solvent from purification zone 14 can be treated in non-BA byproduct removal zone 104, and can be introduced into concentration section 202 via line 38a. Concentration section 202 can operate to remove at least a portion of the solvent contained in the purified byproduct removal feed. The solvent in the purified byproduct removal feed can comprise water and/or acetic acid, as discussed above. Concentration section 202 can remove at least about 30, at least about 45, or at least 60 weight percent of the solvent in the purified byproduct removal feed. Solvent can be discharged from concentration section 202 via line 204.

Any equipment known in the industry capable of removing at least a portion of the solvent from the purified byproduct removal feed stream may be employed in concentration section 202. Examples of suitable equipment include, but are not limited to, one or more evaporators. In one embodiment, concentration section 202 can comprise at least two evaporators. When two evaporators are employed, each one individually can be operated under vacuum at reduced temperature, or can be operated at elevated temperature and pressure. In one embodiment, each evaporator can be operated at a temperature in the range of from about 40 to about 180° C. and a pressure in the range of from about 50 to about 4,500 torr during concentration. Suitable equipment for use as evaporators in concentration section 202 includes, but is not limited to, a heated and agitated tank, a flash evaporator, an advancing front crystallizer, a thin film evaporator, a scraped thin film evaporator, a falling film evaporator, and/or a LIST dryer.

In the embodiment of FIG. 3, a concentrated byproduct removal stream can be discharged from concentration section 202 via line 206. The concentrated byproduct removal stream in line 206 can have a cumulative concentration of non-solvent components (e.g., catalyst components and oxidation byproducts) that is at least about 2 times, at least about 4 times, or at least 6 times the cumulative concentration of non-solvent components in the purified byproduct removal feed stream. The concentrated byproduct removal stream in line 206 can have a cumulative concentration of all of the catalyst components of at least about 1,000 ppmw, in the range of from about 1,000 to about 120,000 ppmw, in the range of from about 2,000 to about 90,000 ppmw, or in the range of from 3,000 to 60,000 ppmw. Additionally, the concentrated byproduct removal stream in line 206 can have a cumulative concentration of oxidation byproducts of at least about 2,000 ppmw, in the range of from about 2,000 to about 900,000 ppmw, in the range of from about 4,000 to about 720,000 ppmw, or in the range of from 6,000 to 360,000 ppmw.

The concentrated byproduct removal stream can be introduced into solid/liquid separation section 208 via line 206. Solid/liquid separation section 208 can separate the concentrated byproduct removal stream into a predominately fluid phase catalyst and BA rich mother liquor and a wet cake. In the embodiment of FIG. 3, solid/liquid separation section 208 comprises mother liquor removal section 208a and wash section 208b. Mother liquor removal section 208a can operate to separate the concentrated byproduct removal stream into the above-mentioned catalyst and BA rich mother liquor and an initial wet cake. The catalyst and BA rich mother liquor can be discharged from mother liquor removal section 208a via line 106. The initial wet cake can be introduced into wash section 208b. At least a portion of the initial wet cake can then be washed with a wash feed introduced into wash section 208b via line 210 to produce a washed wet cake. The wash feed in line 210 can comprise water and/or acetic acid. Furthermore, the wash feed can have a temperature in the range of from about the freezing point of the wash feed to about the boiling point of the wash feed, in the range of from about 20 to about 110° C., or in the range of from 40 to 90° C. After washing the wet cake, the resulting wash liquor can be discharged from wash section 208b via line 212, and the washed wet cake can be discharged via line 112. In one embodiment, the above-mentioned non-BA byproduct rich stream can comprise at least a portion of the washed wet cake.

Solid/liquid separation section 208 can comprise any solid/liquid separation device known in the art. Suitable equipment for use in solid/liquid separation section 208 includes, but is not limited to, a pressure drum filter, a vacuum drum filter, a vacuum belt filter, multiple solid bowl centrifuges with optional counter current wash, or a perforated centrifuge. In one embodiment, solid/liquid separation section 208 can be operated at a temperature in the range of from about 20 to about 170° C. and a pressure in the range of from about 375 to about 4,500 torr during separation.

As mentioned above, the wash liquor can be discharged from solid/liquid separation section 208 via line 212. In one embodiment, at least a portion of the wash liquor in line 212 can be combined with the removed solvent in line 204 to form a solvent rich stream. The solvent rich stream can be withdrawn from non-BA byproduct removal zone 104 via line 122.

FIG. 4 illustrates an embodiment of the present invention where the crude slurry in line 12 can be treated in purification zone 14 to thereby produce a displaced oxidation solvent stream and a purified slurry. The purified slurry can be withdrawn from purification zone 14 via line 16, and the displaced oxidation solvent stream can be withdrawn via line 38. In the embodiment of FIG. 4, at least about 80 weight percent, at least about 90 weight percent, or at least 95 weight percent of the displaced oxidation solvent stream in line 38 can be routed, directly or indirectly, to oxidation zone 10.

In one embodiment of the present invention, at least a portion of the crude slurry in line 12 can be employed as a concentration feed stream. In another embodiment, at least a portion of the purified slurry in line 16 can be employed as a concentration feed stream. The concentration feed stream can be introduced into concentration zone 302. Concentration zone 302 can separate the concentration feed stream into a solvent rich stream and a concentrated isolation feed stream.

Separation in concentration zone 302 can be achieved by any means known in the art that can remove at least a portion of the solvent from the purified slurry. Examples of suitable equipment for use in concentration zone 302 include, but are not limited to, one or more evaporators. In one embodiment, concentration zone 302 can comprise at least two evaporators. When two evaporators are employed, each one individually can be operated under vacuum at reduced temperature, or can be operated at elevated temperature and pressure. In one embodiment, each evaporator can be operated at a temperature in the range of from about 40 to about 180° C. and a pressure in the range of from about 50 to about 4,500 torr during concentration. Suitable equipment for use as evaporators in concentration zone 36 can include, but is not limited to, a simple agitated and heated tank, a flash evaporator, an advancing front crystallizer, a thin film evaporator, a scraped thin film evaporator, a falling film evaporator, and/or a LIST dryer.

The solvent rich stream can be withdrawn from concentration zone 302 via line 304. The solvent rich stream in line 304 can have a concentration of solvent that is at least about 1.1 times, at least about 1.3 times, or at least 1.5 times the concentration of solvent in the purified slurry in line 16. In one embodiment, at least a portion of the solvent rich stream in line 304 can be routed to oxidation zone 10. At least about 80 weight percent, at least about 90 weight percent, or at least 95 weight percent of the solvent rich stream in line 304 can be routed to oxidation zone 10.

The concentrated isolation feed stream can be withdrawn from concentration zone 302 via line 306. In one embodiment, the concentrated isolation feed stream in line 306 can have a concentration of oxidation byproducts that is at least about 1.05 times, at least about 1.2 times, or at least 1.4 times the concentration of oxidation byproducts in the concentration feed stream. Additionally, the concentrated isolation feed stream in line 306 can have a cumulative concentration of oxidation byproducts of at least about 1,050 ppmw, in the range of from about 1,050 to about 280,000 ppmw, in the range of from about 2,100 to about 168,000 ppmw, or in the range of from 3,150 to about 84,000 ppmw.

The concentrated isolation feed stream in line 306 can have a concentration of solids that is at least about 1.05 times, at least about 1.2 times, or at least 1.4 times the concentration of solids in the concentration feed stream. Furthermore, the concentrated isolation feed slurry in line 306 can comprise solids in an amount in the range of from about 20 to about 70 weight percent, in the range of from 25 to 60 weight percent, or in the range of from 30 to 50 weight percent.

In one embodiment of the present invention, the concentrated isolation feed stream in line 306 can be employed as the isolation feed stream introduced into product isolation zone 18. Product isolation zone 18 can separate the concentrated isolation feed stream into a mother liquor, a wash liquor, and an isolated product in substantially the same manner as discussed above with reference to FIG. 1. In the embodiment of FIG. 4, at least about 80 weight percent, at least about 90 weight percent, or at least 95 weight percent of the mother liquor produced in product isolation zone 18 can be routed via line 30 to oxidation zone 10. Additionally, at least about 80 weight percent, at least about 90 weight percent, or at least 95 weight percent of the wash liquor produced in product isolation zone 18 can be routed via line 32 to oxidation zone 10. The treatment and composition of the isolated product in line 20 can be substantially the same as discussed above with reference to FIG. 1.

It will be understood by one skilled in the art that each of the above-described embodiments, as well as any sub-parts of those embodiments, may be operated in a continuous or a non-continuous manner. Non-continuous operations include, but are not limited to, batch-wise operations, cyclical operations, and/or intermittent operations. Additionally, it will be understood that two or more of the above embodiments may be used in combination. For example, in a carboxylic acid production process, a concentration step may be employed both before and after the product isolation step.

In some of the embodiments above, temperature ranges are provided for a specified operation. For each of the above embodiments where a temperature range is provided, the temperature is defined as the average temperature of the substance in the given zone or section. By way of illustration, as discussed above with reference to FIG. 1, the purified concentration feed stream can be treated in concentration zone 36, where the evaporators in concentration zone 36 can be operated at a temperature in the range of from about 40 to about 180° C. This means that the average temperature of the purified concentration feed stream while in the evaporators in concentration zone 36 can be in the range of from about 40 to about 180° C.

Numerical Ranges

The present description uses numerical ranges to quantify certain parameters relating to the invention. It should be understood that when numerical ranges are provided, such ranges are to be construed as providing literal support for claim limitations that only recite the lower value of the range as well as claims limitation that only recite the upper value of the range. For example, a disclosed numerical range of 10 to 100 provides literal support for a claim reciting "greater than 10" (with no upper bounds) and a claim reciting "less than 100" (with no lower bounds).

Definitions

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "including," "includes," and "include" have the same open-ended meaning as "comprising," "comprises," and "comprise."

As used herein, the terms "having," "has," and "have" have the same open-ended meaning as "comprising," "comprises," and "comprise."

As used herein, the terms "containing," "contains," and "contain" have the same open-ended meaning as "comprising," "comprises," and "comprise."

As used herein, the terms "a," "an," "the," and "said" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

CLAIMS NOT LIMITED TO DISCLOSED EMBODIMENTS

The forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A terephthalic acid production process comprising:
   (a) treating a concentration acidic feed stream comprising a solvent and terephthalic acid solids in a concentration zone to thereby produce a solvent rich stream and a concentrated isolation acidic feed stream comprising at least a portion of said terephthalic acid solids; and
   (b) isolating at least a portion of said terephthalic acid solids from at least a portion of said concentrated isolation feed stream in a product isolation zone to thereby produce a mother liquor and an isolated product comprising isolated solids, wherein said isolated solids comprise terephthalic acid particles and oxidation byproducts comprising at least one selected from the group consisting of isophthalic acid (IPA), phthalic acid (PA), trimellitic acid, 2,5,4'-tricarboxybiphenyl, 2,5,4'-tricarboxybenzophenone, 4-CBA, naphthalene dicarboxylic acid, monocarboxyfluorenones, and dicarboxyfluorenones, wherein said oxidation byproducts are formed in said terephthalic acid production process, wherein the kg/hr rate at which said oxidation byproducts exit said product isolation zone with said isolated solids and a portion of said oxidation byproducts are combined with said isolated purified terephthalic acid solids downstream of said product isolation zone is at least 15 percent of said oxidation byproducts generated in said production process; wherein said purified terephthalic acid particles are purified without the use of a hydrogenation step.

2. The process of claim 1, wherein the rate at which said oxidation byproducts exit said product isolation zone with said isolated solids is at least 40 percent of the net make rate of said oxidation byproducts in said production process.

3. The process of claim 1, wherein the rate at which said oxidation byproducts exit said product isolation zone with said isolated solids is at least 60 percent of the net make rate of said oxidation byproducts in said production process.

4. The process of claim 1, wherein the net make rate of said oxidation byproducts in said process is at least 5 kg/hour.

5. The process of claim 1, wherein the net make rate of said oxidation byproducts in said process is in the range of from about 5 to about 20,000 kg/hour.

6. The process of claim 1, wherein said isolated product comprises said oxidation byproducts in an amount in the range of from about 1,000 to about 100,000 ppmw.

7. The process of claim 1, wherein said mother liquor comprises at least a portion of said oxidation byproducts, a catalyst containing at least one multivalent transition metal, and a solvent.

8. The process of claim 7, wherein less than 85 weight percent of said oxidation byproducts in said mother liquor are purged from said production process.

9. The process of claim 1, wherein no purge process is employed in said production process.

10. The process of claim 1, wherein said oxidation byproducts entering said product isolation zone exit said product isolation zone with said isolated product and/or are returned, either directly or indirectly, to a point in said production process upstream of said product isolation zone.

11. The process of claim 1, wherein said concentrated isolation feed stream comprises a concentration of oxidation byproducts that is at least 1.05 times the concentration of oxidation byproducts in said concentration feed stream.

12. The process of claim 1, wherein said concentrated isolation feed stream comprises a concentration of said solids that is at least 1.05 times the concentration of said solids in said concentration feed stream.

13. The process of claim 1, wherein said concentrated isolation feed stream comprises said solids in an amount in the range of from about 20 to about 70 weight percent.

14. The process of claim 1, further comprising subjecting an aromatic compound to oxidation in an oxidation zone to thereby produce a crude product stream comprising crude carboxylic acid particles and at least a portion of said oxidation byproducts.

15. The process of claim 14, wherein at least a portion of said crude product stream is employed as said concentration feed stream.

16. The process of claim 14, further comprising subjecting at least a portion of said crude product stream to purification in a purification zone to thereby produce a purified product stream comprising purified carboxylic acid particles and at least a portion of said oxidation byproducts.

17. The process of claim 16, wherein at least a portion of said purified product stream is employed as said concentration feed stream.

18. The process of claim 16, wherein said purification further produces a displaced oxidation solvent stream.

19. The process of claim 18, further comprising directly or indirectly routing at least a portion of said displaced oxidation solvent stream to said oxidation zone.

20. The process of claim 14, further comprising directly or indirectly routing at least a portion of said mother liquor to said oxidation zone.

21. The process of claim 14, further comprising directly of indirectly routing at least a portion of said solvent rich stream to said oxidation zone.

22. The process of claim 1, further comprising introducing a wash stream into said product isolation zone to wash at least a portion of said isolated solids thereby producing a washed isolated product and a wash liquor.

23. The process of claim 1, further comprising introducing at least a portion of said isolated product into a drying zone to thereby produce a dried isolated product comprising less than 5 weight percent liquid.

24. The process of claim 1, further comprising introducing at least a portion of said isolated product into a solvent swap zone to thereby produce an isolated product wet cake comprising in the range of from about 5 to about 30 weight percent liquid.

* * * * *